United States Patent [19]

Junker

[11] Patent Number: 5,692,517
[45] Date of Patent: Dec. 2, 1997

[54] BRAIN-BODY ACTUATED SYSTEM

[76] Inventor: Andrew Junker, 139 E. Davis St., Yellow Springs, Ohio 45387

[21] Appl. No.: 569,671

[22] Filed: Dec. 8, 1995

Related U.S. Application Data

[62] Division of Ser. No. 1,096, Jan. 6, 1993, Pat. No. 5,474,082.

[51] Int. Cl.$^6$ .................................................. A61B 5/04
[52] U.S. Cl. .................... 128/732; 128/733; 128/731; 128/905; 340/825.19; 341/21; 345/157; 273/438; 434/112; 463/36
[58] Field of Search .................... 128/731–733, 128/905; 434/236, 112, 323, 336, 350; 273/DIG. 28, 438; 345/156, 157; 341/20, 21, 34; 340/825.19, 825.24; 463/36

[56] References Cited

U.S. PATENT DOCUMENTS

| | | |
|---|---|---|
| 2,690,178 | 9/1954 | Bickford . |
| 3,032,029 | 5/1962 | Cunningham . |
| 3,490,439 | 1/1970 | Rolston . |
| 3,604,411 | 9/1971 | Schuler . |
| 3,641,993 | 2/1972 | Gaarder et al. . |
| 3,735,425 | 5/1973 | Hoshall et al. . |
| 3,821,949 | 7/1974 | Hartzell et al. . |
| 3,837,331 | 9/1974 | Ross . |
| 3,875,930 | 4/1975 | Silva et al. . |
| 3,882,850 | 5/1975 | Bailin et al. . |
| 3,916,876 | 11/1975 | Freeman . |
| 3,942,516 | 3/1976 | Glynn et al. . |
| 3,967,616 | 7/1976 | Ross . |
| 3,978,847 | 9/1976 | Fehmi et al. . |
| 3,998,213 | 12/1976 | Price . |
| 4,013,068 | 3/1977 | Settle et al. . |
| 4,031,883 | 6/1977 | Fehmi et al. . |
| 4,031,884 | 6/1977 | Henzel . |
| 4,072,145 | 2/1978 | Silva . |
| 4,149,716 | 4/1979 | Scudder . |
| 4,195,626 | 4/1980 | Schweizer . |
| 4,228,807 | 10/1980 | Yagi et al. . |
| 4,334,545 | 6/1982 | Shiga . |
| 4,354,505 | 10/1982 | Shiga . |
| 4,375,177 | 3/1983 | McCoskey . |
| 4,412,547 | 11/1983 | Callahan et al. . |

(List continued on next page.)

OTHER PUBLICATIONS

Johnston, V. S., "Recognition of Stimulus Displays—An Electrophysiological Analysis", Proceedings of 11th Annual Conference on Manual Control, NASA TMX-62, 464, 1975, pp. 173–178.

Junker, A. et al., "Loop Closure of the Visual–Cortical Response (U)", Summary Report for Period Dec. 1986 to Dec. 1987, Feb. 1988.

"A Comprehensive Treatise on Research in the Area of: Brain Actuated Control", Sep. 1, 1989.

Junker, A. et al., "Brain Actuated Control of a Roll Axis Tracking Simulator", ©1989, IEEE, pp. 714–717.

Wolpaw, J. R. et al., "An EEG-based brain–computer interface for cursor control", Electroencephalography and Clinical Neurophysiology, ©1991, 78: 252–259.

Primary Examiner—Jeffrey R. Jastrzab
Attorney, Agent, or Firm—Wood, Herron & Evans, L.L.P.

[57] ABSTRACT

A method and apparatus for assisting a user to control a device in response to a combination of electroencephalographic and electromyographic potentials. The user selects a number of reference frequencies in a range of from 0.5 Hz to 45 Hz defining a like number of control signals. A digital lock-in amplifier is used with a moving average time window filter to produce control signals which are presented to the user. Control system responsiveness is controlled by adjusting the lengths of the moving average time windows. A phase-locked loop is closed around each control signal and is used to track the shifting frequencies of the control signals. The user is able to sense and control changes in the magnitude and frequency of the control signals in the control of the device. By sensing the changes in the magnitude and frequency of the control signals, the user is able to learn a combination of mental and/or physical activities for which changes in the electroencephalographic and electromyographic biopotentials are correlated to control of the device.

10 Claims, 9 Drawing Sheets

U.S. PATENT DOCUMENTS

| | | |
|---|---|---|
| 4,424,816 | 1/1984 | Callahan et al. . |
| 4,454,886 | 6/1984 | Lee . |
| 4,461,301 | 7/1984 | Ochs . |
| 4,579,125 | 4/1986 | Strobl et al. . |
| 4,595,013 | 6/1986 | Jones et al. . |
| 4,603,703 | 8/1986 | McGill et al. . |
| 4,610,259 | 9/1986 | Cohen et al. . |
| 4,709,702 | 12/1987 | Serwin . |
| 4,776,345 | 10/1988 | Cohen et al. . |
| 4,794,533 | 12/1988 | Cohen . |
| 4,800,888 | 1/1989 | Itil et al. . |
| 4,846,190 | 7/1989 | John . |
| 4,883,067 | 11/1989 | Knispel et al. . |
| 4,928,696 | 5/1990 | Henderson et al. . |
| 4,928,704 | 5/1990 | Hardt . |
| 4,949,726 | 8/1990 | Hartzell et al. . |
| 4,967,038 | 10/1990 | Gevins et al. . |
| 4,974,602 | 12/1990 | Abraham-Fuchs et al. . |
| 4,984,188 | 1/1991 | Kato . |
| 5,002,064 | 3/1991 | Allain et al. . |
| 5,038,782 | 8/1991 | Gevins et al. . |
| 5,119,816 | 6/1992 | Gevins . |

BRAIN-BODY ACTUATED SYSTEM

This application is a divisional of application Ser. No. 08/001,096, filed Jan. 6, 1993, now U.S. Pat. No. 5,474,082.

This application incorporates a Microfiche Appendix of Computer Code comprising two microfiche that include 184 frames of computer code listing found in parent application Ser. No. 08/001,096, now U.S. Pat. No. 5,474,082.

BACKGROUND OF THE INVENTION

1. Field of the Invention

The invention relates generally to the area of non-manual human control of external systems. More specifically, the invention provides a control system with which a user may control an external device by regulating control signals in response to a collective manifestation of electroencephalographic and electromyographic biopotentials. The invention further provides the capability for the user to play music and games and create visual art as training aids for improving system control and for entertainment and relaxation.

2. Summary of the Related Art

Through the years there has been significant research in the area of detecting and observing various electric potentials generated within the human body for medical diagnosis, biofeedback control of mental and physical states, and control of external devices. In that work, it is well-known to detect on the outer surface of the head electroencephalographic ("EEG") biopotentials or brainwaves which demonstrate continuous electrical activity in the brain. The intensities of the brain waves or EEG on the surface of the scalp range from zero to 300 microvolts, and their frequencies range from once every few seconds to 50 or more per second. Much of the time, the brain waves are irregular, and no general pattern can be discerned in the EEG. However, at other times distinct patterns are present. For classification purposes, the EEG has been divided into a number of frequency spectrums. These frequency spectrums can be classified into 'alpha' (8 Hz to 13 Hz), 'beta' (14 Hz to 50 Hz), 'theta' (4 Hz to 7 Hz), and 'delta' (below 3.5 Hz). Activities within the various EEG spectrums have been correlated to states of sleep, relaxation, active thought, etc. Depending on the nature of the activity of interest, it is well-known to detect EEG waves at different areas on the scalp as a function of the part of the brain of interest.

By providing a feedback of EEG biopotentials in a particular EEG spectrum, a subject may be trained to emphasize or de-emphasize an activity associated with that EEG spectrum thereby reinforcing or diminishing the mental and physical state associated therewith. Further, work has been done with a subject to provide a feedback of EEG activity in a particular spectrum, for example, the alpha spectrum of 8 Hz–13 Hz. Using that feedback, the subject learns to control the magnitude of the alpha spectrum to energize a switch or other external device. In other work, through training, a subject is able to generate an alpha biopotential in response to an external stimulus.

A disadvantage in all of the above work is that one measurement site produces only one control. Using multiple bandpass filters or a Fast Fourier Transform algorithm (FFT), the EEG is divided into a number of frequency spectrums. By employing these techniques, users have been able to work with the time varying EEG spectrum magnitudes. While pure EEG signals may be divided into a number of frequency spectra correlated to mental states, it is very difficult to learn to control those spectra and mental states and to maintain such control over time without extensive practice.

It has been suggested that training time can be reduced in the alpha band by phase matching the biofeedback signal to the bandpassed alpha spectrum signal. This is accomplished by delaying the biofeedback signal by one complete cycle. The delay is set as a function of the predetermined dominant alpha peak frequency of the subject. This approach requires that each subject have a predominant alpha peak frequency that can be measured before training. However, one problem is that not all subjects produce spontaneous alpha. A further disadvantage is that this form of phase loop closure will only work for alpha control because theta and beta dominant peaks are not easily predetermined. It also assumes that the dominant alpha peak frequency of the subject wants to be kept constant over a session.

The time varying characteristics of a bandpass filter output can be used to create an estimate of phase information. Likewise the FFT can provide phase measures as well as magnitude measures. Thus phase information can be used as a feedback signal as well as magnitude. However, other than the attempt to create phase matching to an alpha peak frequency as discussed above, there are no instances in the prior art in which use of phase information is successfully incorporated into a biofeedback paradigm.

The contraction of skeletal muscle is preceded by a sequence of rapid changes in the muscle nerve fiber membrane potential. This sequence of potential changes is called an action potential. Each time an action potential passes along a muscle fiber a small portion of the electrical current spreads away from the muscle as far as the surface of the skin. If many muscle fibers contract simultaneously, the summated electrical potentials at the skin may be great. These summated electrical potentials are referred to as electromyographic biopotentials (EMG).

EMG biopotentials have also been detected and used for various forms of medical diagnosis and biofeedback control. Strong EMG biopotentials are usually considered to occur in a range of approximately 100 Hz–3000 Hz; but since the EMG is the summation of numerous action potentials, EMG biopotentials will occur below 100 Hz as well. Therefore, EMG biopotentials contain frequency components between zero and 100 Hz. EMG biopotentials are typically detected at the site of muscle activity, for example, at the jaw to monitor jaw tension or around the eyes to detect ocular muscle activity. EMG biopotentials may be detected for medical diagnostic purposes in which a patient observes their own muscle tension as a biofeedback signal. In addition, EMG biopotentials may be detected for the purposes of activating a switch mechanism to control an external device. Even though EMG biopotentials are somewhat easier to control because they are produced by a physical activity, any use in the prior art work of EMG signals is in response to an averaged magnitude over a spectrum centered at 100 Hz or more. That averaged magnitude is used to control a single activity or switch. Therefore, a limitation of traditional EMG signal processing is only a single channel of control.

Most of the prior work makes extraordinary efforts to work with signals representing either pure EEG biopotentials or pure EMG biopotentials. In the examples of EEG work, the detection and processing of EEG biopotentials in the range of approximately 0.5 Hz–35 Hz includes processing to reject EEG when it contains artifacts of EMG biopotentials. One approach is to inhibit the production of the feedback signal if an undesirable attribute appears in the EEG biopotentials. Another approach is to obtain a multiplicity of EEG and EMG signals and inhibit feedback when any of the EMG signals exhibit undesirable characteristics.

There is a potential problem in using an inhibit approach to deal with an artifact. If a subject simultaneously produces the correct EEG response while producing an inappropriate EMG response, inhibition provides an ambiguous feedback cue. In that case, the absence of feedback due to inhibition suggests to the subject that they are not producing the appropriate EEG response when in fact they are.

Other approaches that attempt to deal with artifacts include: providing subjects with a cross-hair fixation point to limit eye movements, making EEG measurements as far away from potential EMG sources as possible, for example, the occipital and parietal regions of the scalp, and the sensing of and subtraction of the corneoretinal potential from the EEG. All of these approaches have inherent disadvantages. They either provide ambiguous or false feedback cues, require a multiplicity of measurement sites, or they reject the potential usefulness that might be gained by the simultaneous presence of both the EEG and EMG biopotentials. Therefore, even though there has been significant work with EEG and EMG biopotentials for several decades, there have been few practical results.

SUMMARY OF THE INVENTION

To overcome the limitations of current systems, a primary object of the present invention is to provide a control system with which a user may control a device by regulating a plurality of control signals in response to a user presentation of the characteristics of an aggregate of EEG and EMG biopotentials and feedback of the operation of the device. According to the principles of the present invention, an aggregate of the EEG and EMG biopotentials from the user is processed by a digital lock-in amplifier in a phase-locked loop to produce control signals, the magnitude and phase of which may be selectively employed by the user to control devices.

The use of an aggregation of EEG and EMG biopotentials is an important feature of the invention. For electrodes placed on the forehead, the invention detects surface biopotentials resulting from both the EEG and EMG. Investigations with the invention have confirmed the hypothesis that the EMG measured at the forehead is actually a summation of biopotentials from a number of muscle groups such as the eye, frontalis, neck, jaw, etc. Further, that the contributions from the different muscle groups exhibit different and separately detectable frequency spectral characteristics in the 0.5 Hz to 45 Hz range when using the invention. Further, that these different spectral characteristics can be consciously controlled. This ability to control and detect separate muscle groups with the invention, allows immediate user access to multiple controls from one measurement site.

The derivation of multiple controls from the presence of the EMG as well as the EEG at one measurement site, distinguishes the invention from past approaches. In contrast to the prior art, therefore, the invention does not attempt to process either pure EEG related biopotentials or pure EMG related biopotentials, but instead processes a signal derived from an integral combination of both biopotentials. To distinguish the invention from classic EEG signal processing and classic EMG signal processing, the aggregate of EEG biopotentials and EMG biopotentials used by the claimed invention will be defined for purposes herein as a brain-body signal.

The control system first processes the brain-body input signal to produce a filtered input signal which changes in response to changes in the EEG and EMG biopotentials. The user selects a number of reference frequencies in a range of selectable frequencies of from 0.5 Hz to 45 Hz which define a number of control signals in the control system. Each control signal is processed by a digital lock-in amplifier consisting of two quadrature phase detectors. The digital lock-in amplifier samples the filtered input signal and periodically computes X and Y quadrature values at the lock-in reference frequencies of the control signals. Time averaged X and Y quadrature values at the lock-in reference frequencies are periodically computed by lowpass filtering the X and Y quadrature values through moving average time windows. The time averaged X and Y quadrature values are converted to polar form by periodically computing magnitude and phase values at the lock-in frequencies. The user controls the length of the moving average time windows thereby controlling the responsiveness of the control system. The digital lock-in amplifier is extremely effective in detecting periodic signals of low amplitude with a poor signal to noise ratio.

The control system uses a phase-locked loop around each lock-in amplifier to track frequency changes of the reference frequencies of the control signals. This tracking of frequency is driven by the changing phase measures obtained by the lock-in amplifier. An average of the phase of each control signal is computed and used to indicate when the current average phase is leading or lagging a base phase established for each lock-in frequency. A constant phase difference between two signals indicates that they are at the same frequency. A changing phase difference indicates that the two signals may be at different frequencies, and this property is used to create the phase-locked loop. When the phase difference between a control signal and the corresponding lock-in frequency increases, indicating that the control signal is lagging the lock-in frequency, the lock-in frequency is decreased to match or track the decrease in control signal frequency. Likewise when the phase difference increases negatively indicating that the control signal frequency is speeding up relative to the corresponding lock-in frequency, the lock-in frequency is increased to track or follow the increasing frequency of the control signal. In this way, the invention is able to track and follow the changing frequency shifts of each control signal.

The magnitude values and shifting frequency values of the control signals are presented as feedback to the user. The user is able to sense the magnitude and frequency changes in the control signals in response to changes in the EEG and EMG biopotentials resulting from the user's activity. In this way, the user can produce desired control actions with the invention by guiding the changes in their control signal magnitudes and frequency shifts.

The control system has an advantage of using a single measurement site to produce multiple control signals providing the user with extensive capabilities, such as, multichannel, or multi-axis control of devices, the ability to play an electronic musical instrument or video game, the ability to move a cursor about a video display screen, etc. Further, those capabilities are achieved using a single input channel and signal with minimal connections and interference with the user.

Because the invention makes use of both the EEG and EMG manifestations in the brain-body signal, the user may control the mix of the two signals; and the control system has an advantage of responding to users of all levels of control ability. The magnitude and frequency feedback of the control signals to the user include audio and video presentations in user selectable formats. Feedback training paradigms are available to aid in user training. With the control system, a user quickly becomes aware of their connection to the control system and experiences an immediate sense of control through conscious body movements, such as eye movement, jaw tension, deep breathing, etc. In only a few minutes or less, the user is able to consciously direct the control signals which have been generated from the brain-body signal and fed back to the user. With time, users exhibit more subtle control, using smaller amplitude brain-body signals as they begin to minimize the energy required to accomplish magnitude and frequency loop-closure and system control. As the user becomes more proficient, the control system is able to provide the user with expanded and more complex capabilities. Thus, the control system has the advantage that the user should never experience limitations in the control system's ability to respond to their most subtle inputs.

There are several advantages to using the lock-in amplifier technique. Magnitude and phase values about each of the control signal lock-in frequencies of interest may be quickly computed, thereby permitting the responsiveness of each measure to be individually adjusted. If the time between when a user generates a signal and when the user receives a measure of that signal is too long, the user will not experience a sense of connection with the feedback device. Signals in the theta band change more slowly than signals in the alpha band, which change more slowly than signals in the beta band. The invention accommodates those variations by permitting different values of responsiveness to be set for each control signal. Proportionally decreasing responsiveness in the lower frequency band provides an additional benefit of increasing the frequency selectivity in those bands where it is needed.

Another important capability of the lock-in amplifier as incorporated in the invention is the ability to change a control signal lock-in frequency at any time and independently of the other control signal lock-in frequencies. In contrast to other signal transform techniques, such as FFT, a lock-in frequency can be shifted up or down any amount at any time. The invention makes use of this capability to create phase-locked loops about each of the brain-body control signals.

These and other objects and advantages of the invention will be apparent to those skilled in the art in light of the present disclosure including the accompanying drawings, the detailed description of the invention and the appended claims.

DETAILED DESCRIPTION

Figure 1:
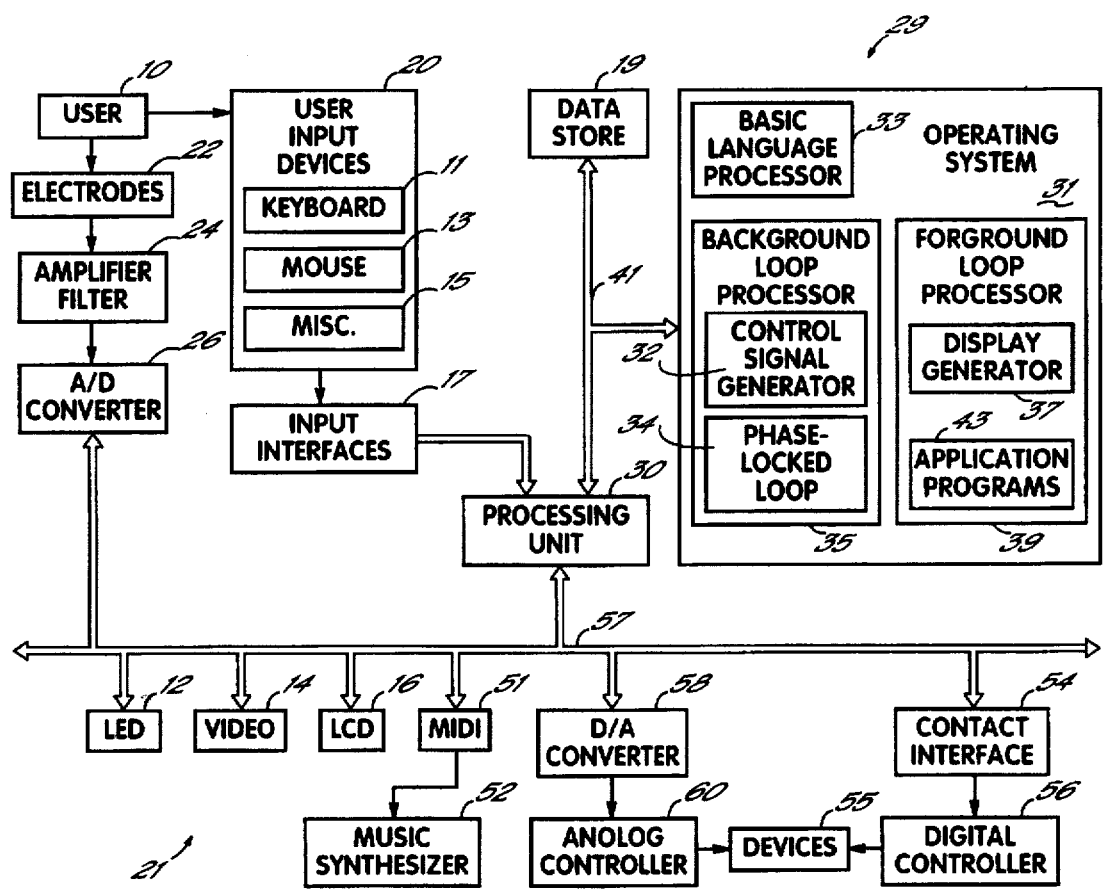
FIG. 1 is an overall block diagram of the control system of the invention.

A system schematic diagram of the control system of the invention is presented in FIG. 1. A user 10, for example, a human, interacts with the control system 29 through control of their brain-body signal detected by electrodes 22, through other input devices 20, such as a keyboard 11, mouse 13, or voice activation 15, and through information fed back to the user from output mechanisms 21, such as, by audio and visual means and the operation of devices. The input signals from the input devices 20 are connected to a microprocessor processing unit 30 by means of input interfaces 17. Once the system is set up for a user, their brain-body connection may be the sole operative input to the control system. Thus the invention can be used by differently abled people. The brain-body signal is preferably detected at the forehead, however other locations may be used. Preferably, three electrodes which include two signal lines and a neutral line are attached to the forehead of the user. The physical relationship of the two signal electrodes to the neutral or ground electrode is a function of the application of the system. For example, the neutral may be placed at a position between the other two electrodes. This configuration has been found to provide the best sense of balance by users for most loop closure activities.

The preferred electrodes are not standard EEG electrodes which have a relatively small surface area for more localized input. But instead, the preferred electrodes have a larger surface area, for example, electrocardiographic ("EKG") electrodes, which will pick up more of the EEG potential. Therefore, the signal will not be localized but will contain more signal averaging. The three electrodes are mounted at selectable positions in a head band. When worn by a user the electrodes are applied to the forehead. The electrodes may be silver/silver chloride hydrogel disposable electrodes designed for resting EKG use, commercially available from NDM. As will be appreciated, a supplemental tube gel may be used to reduce the electrical resistance of the junction between the electrode and the user.

The amplifier and filter system 24 amplifies the brain-body signal output from the electrodes. The amplifier and filter system has a gain of approximately 50,000 and provides a bandpass filter with a bandwidth of approximately 0.5 Hz to 45 Hz. The amplifier may be a Grass model P5 series A.C. pre-amplifier and Grass RPS107 power supply. The filter may be a Krohn-Hite model 3750 bandpass filter.

The amplified and filtered brain-body input signal representing an aggregate of EEG and EMG biopotentials is connected to an analog to digital ("A/D") converter 26. The connection to the A/D converter 26 may be solid wires with electrical isolation means, infra-red transmission, radio transmission or any commercially available serial bidirectional communication link. An A/D converter such as model ADA 1100 commercially available from Real Time Devices may be used. The A/D converter 26 contains an internal 100 Hz clock which is used to sample the analog brain-body signal at a rate of 100 samples per second. The digital brain-body signal is stored in data store 19 with each sample.

The brain-body signal processing may be accomplished within a commercially available personal computer having a processing unit 30 comprised of a 386 Intel processor and math coprocessor with a 33 MHz clock. Operating system 31 is comprised of software programs including the standard DOS based operating programs and BASIC language processor 33. Other programs within the operating system 31 also include a background loop processor 35 and a foreground loop processor 39 which are unique to the control system of the claimed invention. The background loop processor 35 reads the brain-body signal from the A/D converter 26 and uses a digital lock-in amplifier provided by control signal generator program 32 to produce control signals at reference frequencies the user has chosen from a range of selectable frequencies. Next a phase-locked loop program 34 forms a phase-locked loop for each control signal. The phase-locked loop permits the control system 29 to track the predominant frequencies of the brain-body signal within each selected control signal reference frequency band. Generation of the control signals and the phase-locked loop are controlled by the same 100 Hz clock that controls the A/D converter 26. Gain and responsiveness of the control system are selectable by the user via the user input devices 20. The processing unit 30 transmits data between it, the operating system programs and the data store over an internal data bus 41.

A display generation program 37 within the foreground loop processor 39 uses the brain-body signal and generated control signals as a basis for the presentation of various audio and visual feedback to the user. Depending upon the task being performed by the user, different visual displays may be incorporated, for example, a video display terminal 14, an LCD display 16, or an LED display 12 may be used. Further, the foreground loop processor 39 permits the user input devices 20, such as a mouse or keyboard, to be used to select various application programs 43 for execution. User application programs include a play music program, a compose music program, computer game programs, cursor control programs and mouse programs. The data store 19 stores data associated with the execution of programs within the background loop processor 35 and foreground loop processor 39. External devices 55, such as a wheel chair, cursor control, music synthesizer, a sailboat, etc, can be connected to the control system 29 and operated by the control system via a contact interface 54 and associated switch closures within a digital controller 56 or a digital to analog converter 58 and an analog controller 60. The processing unit 30 communicates with the devices 55 and output devices 21 over an input/output bus 57 which may be an expansion bus typically found in personal computers.

Figure 2:
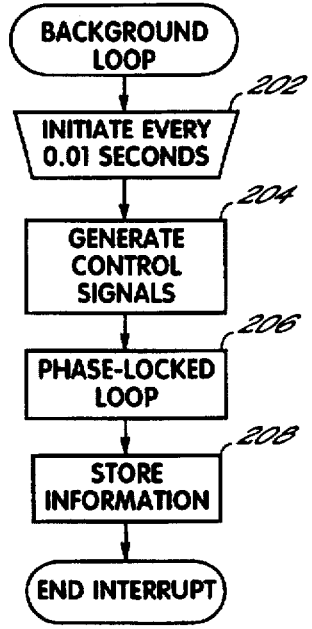
FIG. 2 is a flowchart of a process for executing the background loop program of the control system.
Figure 3:
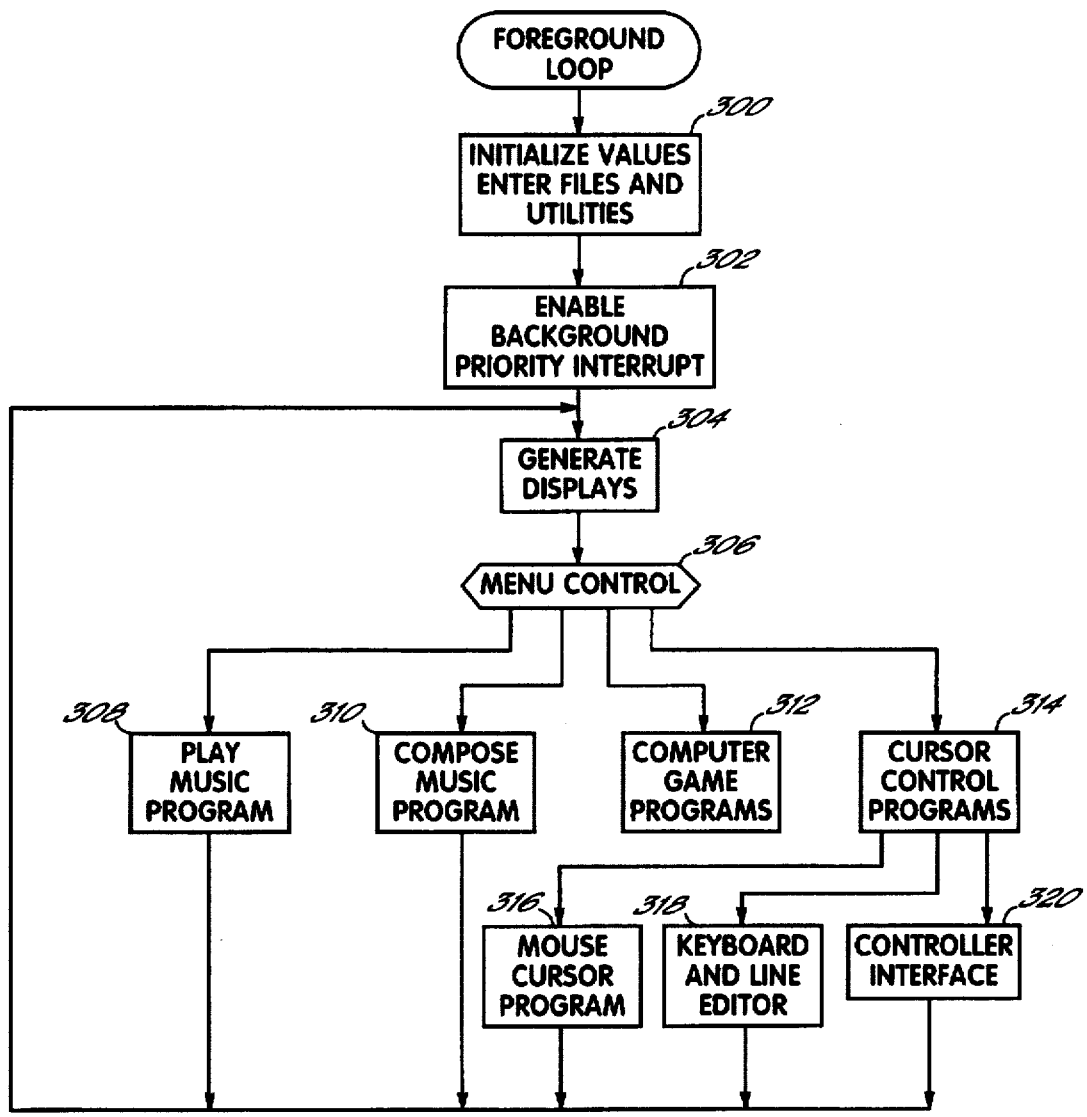
FIG. 3 is a flowchart of a process for executing the foreground loop program of the control system.

FIGS. 2 and 3 illustrate the two principal processing loops executed by the software in processing unit 30. The background loop processor of FIG. 2 is a time dependent priority interrupt processor and is executed every 10 milliseconds. The time of execution may be controlled by an external or internal clock and preferably is driven by the same 100 Hz clock that controls the sampling of the A/D converter 26. The foreground loop processor of FIG. 3 is not time dependent. The foreground loop can be incorporated into the background loop resulting in both programs being executed once every 10 milliseconds. In the disclosed embodiment, the foreground loop continuously executes while the background loop interrupts every 10 milliseconds. In other embodiments, the background loop may be executed by an independent processor, and the foreground simply reads the computed values as required.

When the control system is turned ON by the user, the foreground loop of FIG. 3 is entered. The program at step 300 first initializes values and reads the required files and utilities. The default values for ten reference frequencies are in a predetermined range of from 0.5 Hz to 45 Hz, and those ten reference frequencies defining the control signals are read from data files. At step 302, the foreground loop processor enables the priority interrupt for the background loop processor thereby permitting a background loop interrupt generated every 10 milliseconds at step 202 of FIG. 2 to interrupt the foreground loop. With each interrupt, a lock-in amplifier is used to determine the magnitude and phase values for each control signal at step 204. At step 206, a phase-locked loop is used to determine changes in the phase of the control signals, and the phase changes of the control signals are used to change the reference frequencies. The final step 208 of the background loop program is to store these values for future use by the foreground loop processor.

Upon completion of the background loop processor, the control signals are fed back to the user via audio and/or video presentations, step 304 of FIG. 3. Via feedback presentations of control signal magnitudes and reference frequencies, the user is able to sense how changes of EEG and EMG biopotentials effect the control signals. The response of the user determines the flow through the remainder of the foreground loop. Once entered, the foreground loop processor 39 continuously loops back to the display step 304 which updates the user presentations based on the magnitude and phase signal values computed from the last interrupt. The user is then able to control functions of a device in response to the control signals. More specifically, using menu displays, the user modifies the performance of the control system during each iteration of the foreground loop processor. The user chooses whether to execute a play music program 308, a compose music program 310, a computer game program 312, or a cursor control program 314. Under the cursor control program 314, the user can choose to work with the mouse program 316, a keyboard/line editor program 318, or the controller interface 320.

The play music program 308 permits the user to play music on an electronic musical instrument with control signals in a manner similar to using fingers on a keyboard. As the user plays the music and senses, by sight and hearing, the control signal presentations and the notes being played, the user is able to become aware of the relationships between the sensed characteristics of the control signals and their brain-body activity. Additionally, the user is able to learn about music from the displays. While playing music, the user can also choose to display a kaleidoscope which presents a changing colored pattern. The turning ON and OFF, screen location and assignment of color attributes to the display pixels corresponds to the control signal magnitude and phase values. Playing music has the benefit of providing the user with a rich and pleasing audio biofeedback training paradigm. A compose music program 310 permits the user to compose new music. Music may be composed specifically to aid the user in the exploration of their brain-body connection in designated frequency bands of interest. Examples of this include such capabilities as learning to increase alpha or theta band activity while lowering beta band activity. Since the user simultaneously receives biofeedback information about brain and body activity, the control system permits the user to explore the relationship between body biopotentials, EMG, and brain biopotentials, EEG, in these bands.

Computer game programs 312 may be played with the control system of the invention. As well as being entertaining and challenging, the games provide opportunities for the user to learn to work with the control signals derived from their brain-body signal. The ability to consciously regulate one control signal coupled with an opportunity window display, to be subsequently described, or the conscious regulation of two control signals simultaneously permits the user to interface with the cursor movement programs 314 and mouse cursor programs 316. With the mouse cursor capability, the user is able to access the control signal actuated keyboard and line editor routines 318. The same approach that is used for cursor control in the control system is used in the controller interface program 320. The ways in which controls signals are used for multiaxis control and the implementation of an opportunity window to achieve multiaxis from one control signal are discussed below.

Figure 4:
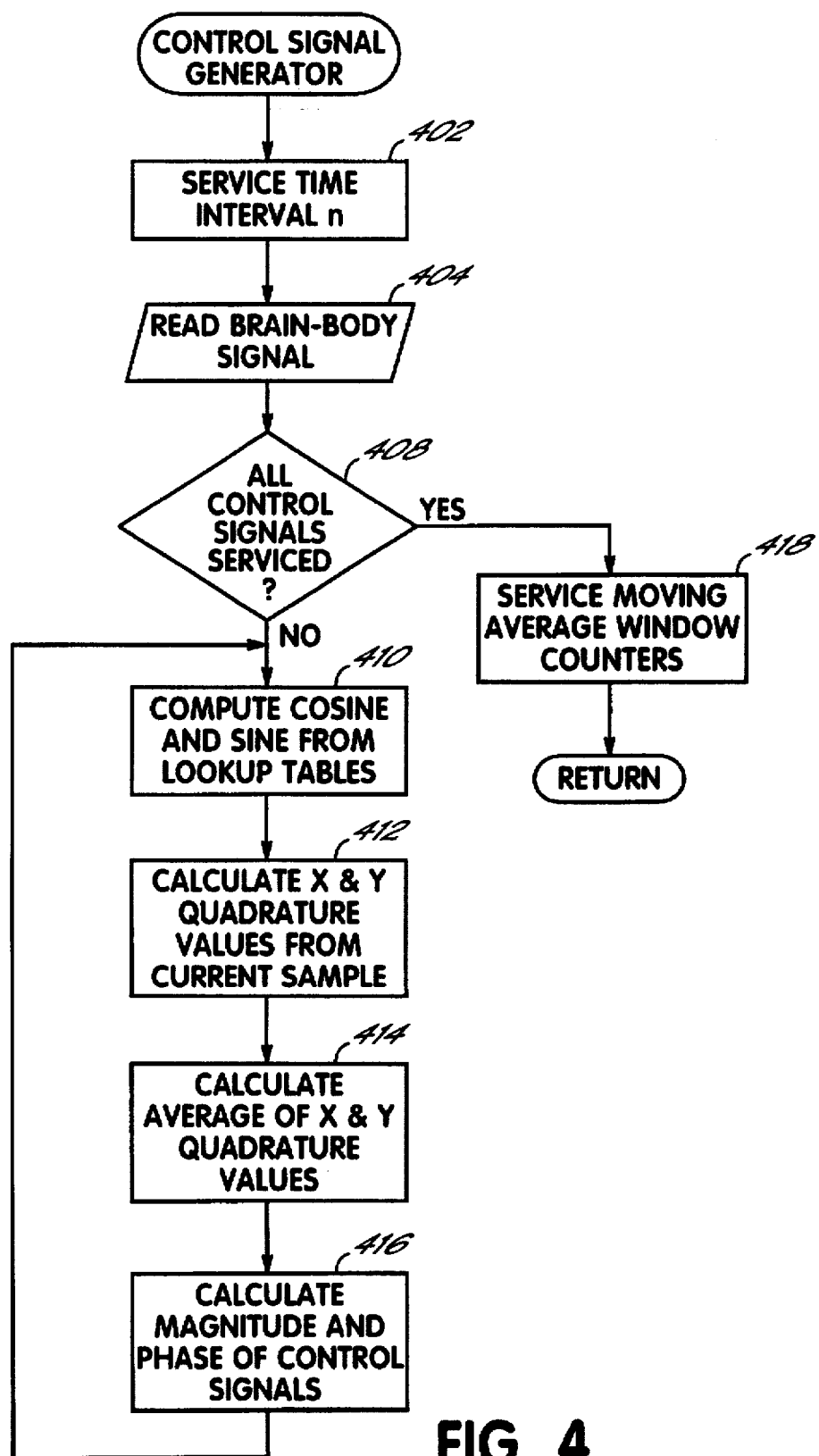
FIG. 4 is a flowchart of a process for generating control signals.

FIG. 4 is a flowchart of the control signal generator program executed at step 204 of FIG. 2 of the background loop and illustrates a process for generating control signals from sampled brain-body signals. The brain-body signal output from the A/D converter 26 is sampled at successive sample times, for example, once every 10 milliseconds, using the 100 Hz clock within the A/D converter to produce sampled input signals. Consistent with frequency sampling theory, the sample rate of 100 Hz is more than twice 45 Hz, the highest brain-body signal frequency of interest. The control system generates a time history for each control signal by averaging the quadrature values of each control signal over respective moving average time windows.

To calculate the quadrature values of the brain-body signal required to implement the digital lock-in amplifier, sine and cosine values must be determined over a range of from zero degrees to 360 degrees. The control system utilizes a table of sine and cosine values to increase the processing speed. To implement the table, one cycle of a full sine wave has been divided into N increments; and sine and cosine values for each of the N increments is stored in the table. The increment size of the table is used to define the angular resolution, that is, fundamental frequency, of the control system. A value of N=1600 increments has been arbitrarily chosen to reduce memory storage requirements for the table. Given a sample rate of 100 Hz, or 10 milliseconds, this results in a fundamental frequency, $\Delta f=0.0625$ Hz. The sin and cos values for each table position are computed and stored during the initialization phase, step 300 of FIG. 3 as follows:

$$\text{table } \cos_n = \text{COS} 2\pi \left( \frac{n}{N} \right)$$

$$\text{table } \sin_n = \text{SIN} 2\pi \left( \frac{n}{N} \right)$$

where

N=Maximum table size, and n=current value of a time based index from 1 to N.

The control signal generation program of FIG. 4 begins with the servicing of a time index n at step 402. The index is incremented by one with each iteration up to a cumulative value of N, or 1600 iterations. After N iterations, the index is set back to one. With each iteration, the sampled digital brain-body signal is read at step 404 of FIG. 4 and held in a buffer store.

At decision step 408, an internal counter permits steps 410–416 to iterate a number of times equal to the number of control signals selected by the user. With the disclosed embodiment, up to ten control signal frequencies may be selected and computed. The selected frequencies of the control signals are specified in terms of harmonics of the fundamental frequency, as follows $$H_i = \frac{Cf_i}{\Delta f}$$

where $Cf_i$=frequency of the current control signal being processed, $\Delta f$=fundamental frequency, and $i=i_{th}$ control signal.

The specific sine and cosine table position p from which sin and cos values are to be read is determined by $$\text{table position } p = n_i(H_i + f_{s_i}) + Ph_{s_i}$$

where $f_{s_i}$=frequency shift from Phase-Locked Loop routine block 520 or block 522, and $Ph_{s_i}$=previous table position, updated each time a new frequency shift is requested by the phase-locked loop.

if $p \leq N$, then operating within first harmonic and may go directly to table position p; but if $p > N$, then must extract the number of harmonics as follows:

$$\text{table position } p = n_i H_i - \left[ \text{integer of } n_i \left( \frac{H_i}{N} \right) \right] N$$

Each time a shift in the lock-in frequency of a control signal is requested, the phase shift value is assigned the previous table position value; and the time based index is reset to n=1. Resetting the time based index and defining a new phase shift value creates a smooth transition from one lock-in frequency to the next.

At step 410, using the above, sin and cos values for the lock-in frequencies of the control signals at the current time based index are read from the table. Using those sin and cos values, the X and Y quadrature values at the lock-in frequency of the control signal being processed are computed for the current sample of the brain-body signal at step 412, as follows:

$$X_{quad_i} = (bb_n)(\cos_p)$$

$$Y_{quad_i} = (bb_n)(\sin_p)$$

where $bb_n$=brain-body signal at the current index, and $\sin_p$, $\cos_p$=sine and cosine table values.

Next, at step 414, the average values of the X and Y quadrature values are computed. First, the X and Y quadrature values are added to respective X and Y moving average time window filters. The user is able to adjust control system responsiveness for each control signal to match the user's perceptions. That adjustment is made by the user selecting the lengths of the moving average time windows in a range of from 50 samples to 300 samples. The length of both the X and Y moving average time windows is the same and is adjusted in unison. Given a 100 Hz sample rate, the range of adjustment of the moving average time windows represents a bandwidth about the center frequency of from 2 Hz to 0.33 Hz. Therefore, if the user selects a more responsive system, the control system reduces the length of the moving average time windows by reducing the number of samples in the windows. As the system becomes more responsive, the lock-in frequency bandwidth increases; and the control system has less resolution about the selected lock-in frequency. Alternatively, if the user selects a less responsive system, the control system lengthens the moving average time windows by increasing the number of samples in the windows. With a less responsive system, the bandwidth about the lock-in frequency decreases, and the control system has greater resolution about the selected lock-in frequency. At step 414, for each of the X and Y moving average time window sums, the oldest X and Y quadrature values are subtracted from their respective sums, and the new X and Y values are updated and added to their respective sums. The average X and Y quadrature values are then calculated by dividing each of the X and Y quadrature sums by the size of the time window, that is, the total number of samples used for averaging as determined by the responsiveness selected by the user. Therefore, the X and Y quadrature average values are calculated as follows:

$$X_{sum_i} = X_{sum_i} - X_{l,w_i} + X_{quad_i}$$

$$Y_{sum_i} = Y_{sum_i} - Y_{l,w_i} + Y_{quad_i}$$

$$X_{l,w_i} = X_{quad_i}$$

$$Y_{l,w_i} = Y_{quad_i}$$

$$X_{avg_i} = \frac{X_{sum_i}}{W_i}$$

$$Y_{avg_i} = \frac{Y_{sum_i}}{W_i}$$

where $W_i$=size of the $i_{th}$ time averaging window, and $w_i=i_{th}$ time average window index from 1 to $W_i$.

The user also has the ability to set and adjust the value of a gain to be applied to each of the control signals, and those control system gain values are stored. At step 416, the stored control signal gain values and the averaged X and Y quadrature values are used to compute time averaged magnitude and phase values of the brain-body signal corresponding to the control signal lock-in frequencies being generated for the current sample of the brain-body signal as follows:

$$mag_i = G_i \sqrt{(X_{avg_i})^2 + (Y_{avg_i})^2}$$

$$phase_i = \arctan \frac{Y_{avg_i}}{X_{avg_i}}$$

where $G_i$=user selected gain for $i_{th}$ control signal

Even though the arctangent function is recited, other identities may be used to define the phase. It is typically defined in a range of ±90 degrees.

After the magnitude and phase values for all the control signals have been evaluated for the current time index, n, as detected by decision block 408, the moving average time window counters are serviced at process step 418. As previously discussed, the lengths of the time windows may be adjusted by the user; and the control system monitors the user settings and adjusts the length of the moving average time windows at step 418.

The lock-in amplifier approach permits different window lengths for each control signal. If the user does not choose to change these values, the invention defaults to values that have been chosen to improve high frequency responsiveness and low frequency selectivity at the same time. Window widths relative to the center or 5th lock-in frequency are defined at the start of the program as follows:

$$W_i = W_5 \sqrt[8]{\frac{H_5}{H_i}}$$

Figure 5:
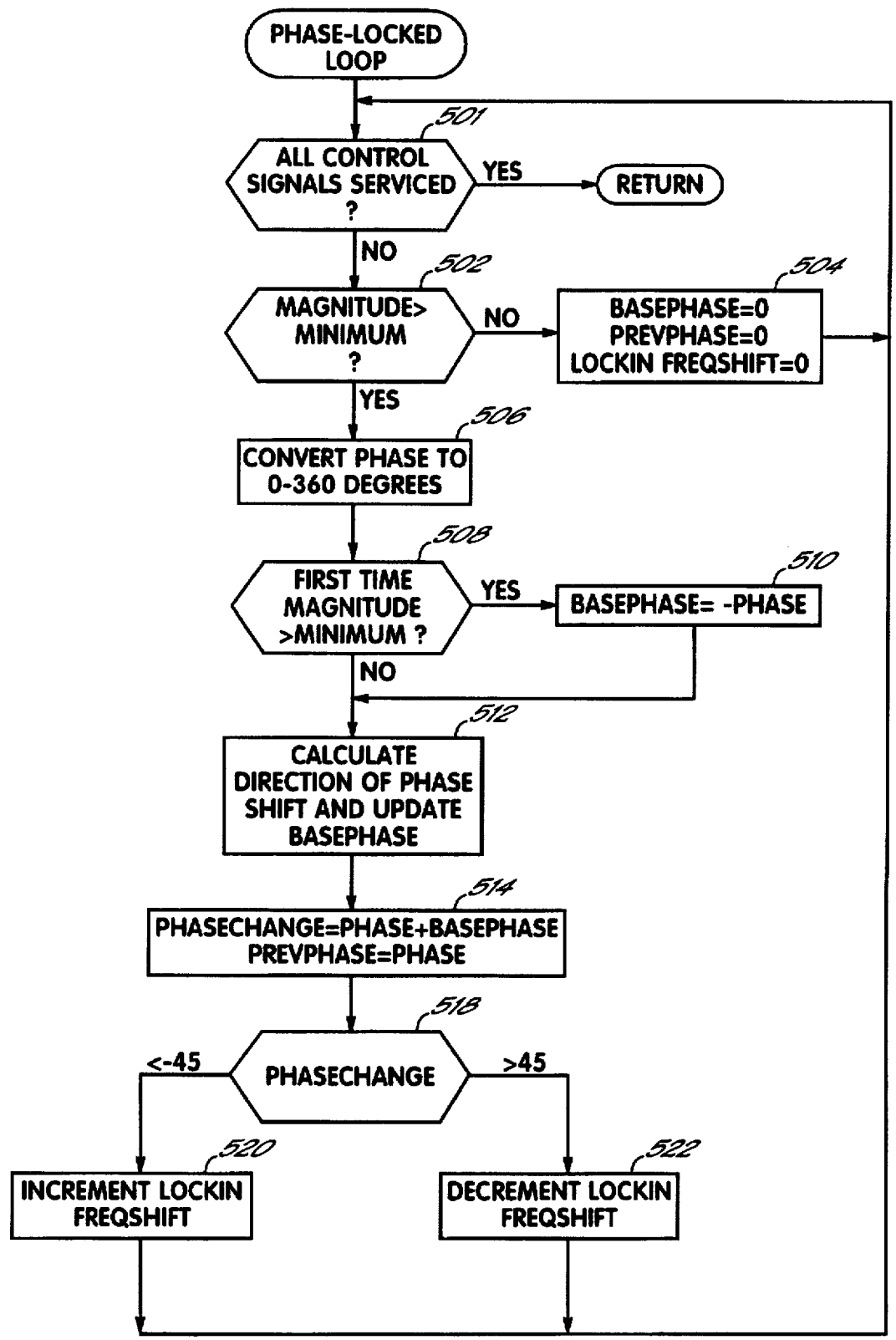
FIG. 5 is a flowchart of a process for executing a phase-locked loop program to adjust the phase of the control signals.

After the control signal magnitude and phase values have been determined, the phase-locked loop, step 206 of FIG. 2, of the background interrupt routine is executed. Referring to FIG. 5, the phase-locked loop program must be executed a number of times equal to the number of control signal frequencies selected by the user. Therefore, at step 501, the process checks to determine whether all the control signals have been serviced. If not, at decision step 502, the process determines whether the magnitude of the control signal being considered is greater than a user definable minimum value. If not, the base phase, previous phase, and lock-in frequency shift values are reset to zero, at step 504, in preparation for when the magnitude does exceed the minimum. A minimum magnitude test is preferred to eliminate those signals which cannot be distinguished from noise, and the phase-locked loop routine will only process control signals having a magnitude greater than the minimum. Typically, an acceptable minimum signal magnitude is at least 5% of the maximum signal magnitude. In the absence of a user selection, the minimum is defaulted to 5%.

If the control signal is greater than the minimum, the phase for that control signal is adjusted to a range of between 0 degrees and 360 degrees per step 506. It should be noted that the calculated X and Y quadrature values are vector quantities. Therefore, the signs of the quadrature values may be used to identify in which quadrant of a 360 degree unit circle the vector is located. The ±90 degree phase values, which were determined at step 416 of FIG. 4, may be used to define the specific vector location in the identified quadrant.

If this is the first time that a control signal is greater than the minimum, the lock-in frequency phase is matched to the control signal phase. At step 510, a base phase, which is a reference phase, is established by setting its value equal to the negative of the present phase value of the control signal for the current sample of the input signal. For the first time processing of that control signal, the remainder of the routine of FIG. 5 provides no additional processing. Therefore, with the first iteration, the control signal being processed by the phase-locked loop is brought into phase with the current phase of the brain-body signal at that lock-in frequency. During a subsequent iteration of FIG. 5 in the processing of another sample of the input signal, if that control signal has a magnitude greater than the minimum, the process moves through step 508 to step 512.

At step 512, the direction of phase change from a previous phase value to the present phase value is determined. The control system assumes that the direction of phase change is defined by the minimum path, that is, the shortest distance around a 360 degree unit circle, in moving from the previous to the present phase values. If the minimum path is defined by counterclockwise movement around a 360 degree unit circle, the current phase value is assumed to be lagging the previous phase value. Conversely, the current phase value is interpreted as leading the previous phase value if a clockwise movement results from the minimum path. If the minimum path results in crossing the 0/360 degree point of a unit circle, the base phase value is adjusted by adding or subtracting 360 degrees according to whether the current phase is lagging or leading, respectively.

At step 514, a phase change of the current phase value relative to the base phase value is computed by algebraically adding the current phase value to the adjusted base phase value. The phase change represents a difference between the base phase value and the current phase value. Further, the previous phase is set equal to the current phase value in preparation for the next iteration.

At step 518, the phase change value of the current control signal is tested to determine whether the current control signal is lagging or leading the base phase value of the current control signal by a predetermined arbitrary minimum amount, for example, ±45 degrees. If the phase change is detected to be greater than a predetermined arbitrary minimum amount, for example, ±45 degrees, a frequency change of the lock-in reference frequency of the control signal is initiated. This is accomplished by incrementing or decrementing a frequency shift at steps 520 and 522, respectively. If the control signal is leading as indicated by the phase change value being more negative than −45 degrees, the lock-in frequency is incremented at step 520 to cause the lock-in frequency to be shifted up to catch-up to the control signal. A positive value of phase change greater than 45 degrees indicates that the control signal is lagging the reference value, and the lock-in frequency is decremented at step 522. Preferably the lock-in frequency is shifted up and down in multiples of a predetermined frequency increment, for example, the fundamental frequency, $\Delta f$. The lock-in frequency shift is accomplished at step 410 of FIG. 4 by assigning the phase shift value the immediately prior table position value, and resetting the time based index to n=1. Resetting the table position and defining a new phase shift value creates a smooth transition from one lock-in frequency to the next. As will be appreciated, other phase change tests may be implemented. For example, a test may be made to determine whether the phase change differs from the base phase value by 90 degrees, 135 degrees, etc., and the lock-in frequency shifted by appropriate multiples of the fundamental frequency.

A phase-locked loop can also be employed with an FFT. However, with the FFT, the fundamental frequency is inversely related to the responsiveness of the algorithm. Thus, to obtain responsiveness comparable to what is possible with the lock-in amplifier, would result in frequency steps of no less than 0.78125 Hz (based upon a 128 point transform and a 100 Hz sample rate). Therefore, the equivalent FFT phase-locked loop can not function at as fine a level as is possible with a lock-in amplifier based phase-locked loop. Usually, no more than four steps up or down are needed to create an effective phase-locked loop. The shift in the lock-in phase is fed back to the user through visual and audible displays as will be hereinafter described.

Figure 6:
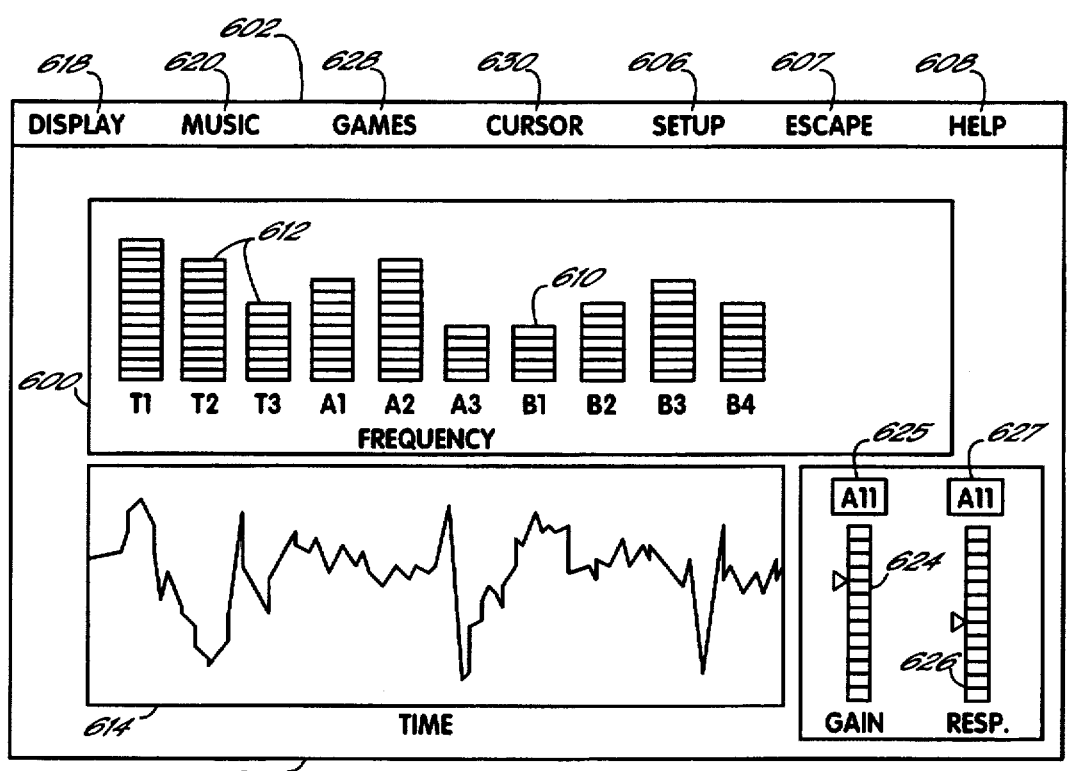
FIG. 6 is a recreation of a brain-body time history and control signal display.

FIG. 6 illustrates the primary screen of the invention by which the control signals are presented to the user by being displayed on video monitor 14 of FIG. 1. User interaction is provided along the top area 602 of the screen 604 which contains various pull-down menus. Below the menu area 602, the control signals derived from the brain-body signal are simutaneously presented as a series of bar graphs on a graphic display 600. Each bar 612 represents a selected control signal, and the length, or height, of the bar represents the magnitude of the respective control signal. The system provides the user with up to ten frequency spectra, three in the theta, three in the alpha and four in the beta frequency range. The theta bands are displayed in blue, the alpha bands in green and the beta bands in red. While the control system is running and the phase-locked loop is functioning, the colors of the bands shift in color shades to indicate to the user the up and down shifting of the lock-in frequencies as they follow the frequency shifting of the user's control signals. The screen 604 also displays the time history 614 of the user's brain-body signal. The screen 604 further displays two slide controllers 624 and 626 which allow the user to adjust gain and responsiveness, respectively, of all or any selected control signal. Using the control signal selection window 625 and the gain slide controller 624, the user is able to change gain values for all or any all of the control signals. Using the control signal selection window 627 and the response slide controller 626, the user can tune the responsiveness of the system to match the characteristics of the tasks being performed. For example, the playing of video games usually requires a high degree of responsiveness and less selectivity, while the playing of certain musical pieces wants a higher degree of selectivity and a slower responding system.

Using the mouse or keyboard devices 20 of FIG. 1, the user can access the various menu selections. The display menu 618 allows the user to select various time history displays such as the brain-body signal illustrated, control signal magnitudes, control signal phases, etc.

Figure 7:
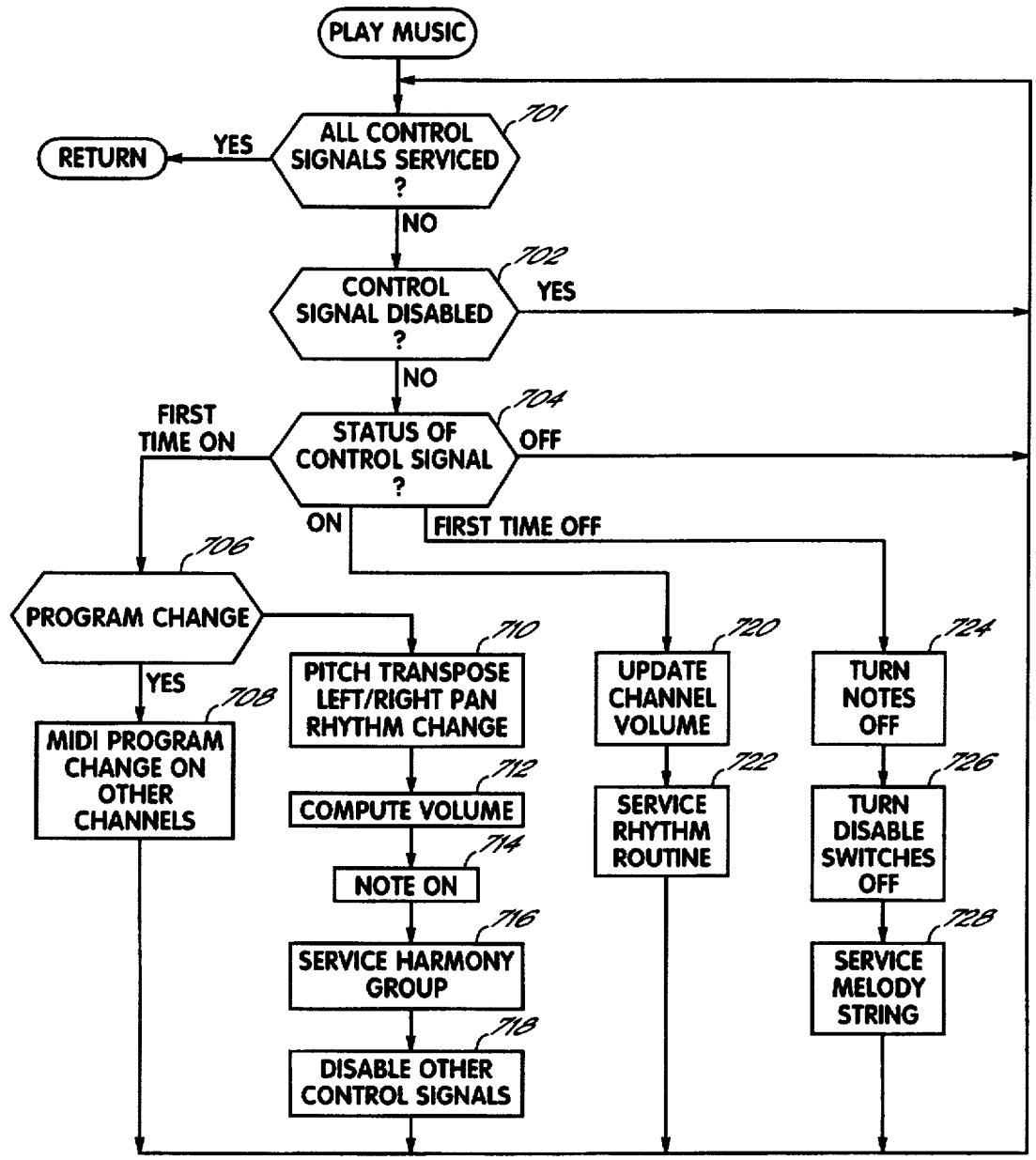
FIG. 7 is a flowchart of a music program and MIDI code generation routine.

The music menu 620 allows the user to select the compose music routine or the play music routine of FIG. 7. The play music routine presents a first screen having displays similar to FIG. 6, that is, a time history of the control signal and bar graphs with on-off musical switches included. The play music musical routine also provides a training screen 802 illustrated in FIG. 8, and a kaleidoscope display, not shown. The game menu 628 permits the user to select and play training games. The cursor menu 630 allows the user to either work with the mouse cursor, use the cursor controlled keyboard and line editor, or work with the controller interface for the control of external devices. The setup menu 606 allows the user to customize the control system to individual needs. One setup menu selection allows a control mode in which the control system may be setup in response to control signals generated by the brain-body signal. In this way, differently abled users can be initially setup by an attendant and then left on their own with the invention. Within the setup menu, the default values of the control signal reference frequencies may be changed. Since the system is digital, the selection and modification of control signal frequencies is based on discrete increments defined by a fundamental frequency. Further, as with any frequency responsive or resonant system, to fully exploit the capabilities of the control system, the selection of the control signal frequencies should consider the influence of harmonic relationships between chosen frequencies of the control signals. The frequencies should be chosen so that the control system signal processing minimizes the first order harmonic distortions. Therefore, the above considerations may impose some constraints on the selection of control signal frequencies and the separation between selected frequencies. Those constraints may be implemented as defaults in the control system or may be overridden by the user. The escape menu 607 allows a user to return to a previous display or program status at any time. The help menu 608 provides access to a user's manual.

Once computed, the magnitudes and frequency shift values of the control signals provide feedback links between the user, the control system program and any associated devices. By controlling these values, the user controls the system. To make use of the changing magnitude levels, user selected predetermined ON and OFF switch levels are defined for each control signal. The ON and OFF switch levels represent predetermined control signal magnitudes which are effective to control functions on external devices. When the user causes the magnitude of a control signal to exceed the associated ON switch level, the control system responds with an appropriate function. In the music program, for example, this may result in a note being turned ON; or if the note is already ON, the volume tracking the magnitude of the control signal. Alternatively, the cursor control program may use the control signal switch to direct cursor movement in a desired direction or to effect a switch closure associated with the operation of an external device. When the user causes the control signal magnitude to be equal to or less than the OFF switch level, generally the opposite function is initiated. For example, a note is turned OFF, a switch is opened, etc. Although different control signal magnitudes for the ON and OFF switch functions are preferred, the ON and OFF switch functions may be achieved by determining whether the control signal magnitude is greater or less than a single predetermined switching level.

The shifting of the control signal lock-in frequencies may be used as controllers in much the same way that the changing magnitudes are used. The speeding up and slowing down of the frequencies are natural controllers for providing direction in the music routine. The frequency shifting is used to actuate transposition, rhythm changes and left/right pan or stereo balancing. In the case of cursor movement and control of external devices, the magnitude and corresponding frequency shifting allow two axis control. For example, the magnitude is used for up/down movement and the frequency shifting is used for left/right movement. The system permits the user to control a function for an external device in response to one or any predetermined number of incremental frequency shifts of the lock-in frequency.

The music program allows the user to interface with a synthesizer to play music by generating code that uses the MIDI standard. The music routine makes use of MIDI functions to create a structure which when 'played' by the user with their control signals, produces a musical experience having content, form and direction. Songs are first composed by the user or the user can request previously composed songs. The composed songs are structures or templates through which the user plays or creates music by changing the magnitude and frequency of their control signals.

Composing a song involves creating a template that can then be accessed by a user to play music. Within the template, the composer specifies ON and OFF switch levels for each control signal that is to be used for playing the musical piece. The notes to be played by each control signal and what channels to map them to in the synthesizer are specified. Harmony groupings and the notes for melody strings for the different control signals are also specified. To allow the presence of opposing harmony groups and melody strings in the same piece, a disabling capability is available. The composer specifies what other control signals are to be disabled when a given control signal exceeds it's ON switch. The responsiveness of each control signal can be specified by the composer in terms of the length of the moving average time window filter for that control signal. The mapping of voices to MIDI channels is specified as part of the composing process, as are channel volumes. Rhythm in the form of note accenting can be specified for selected control signals as part of the composing process. The frequency shifting values computed by the phase-locked loop routine can be used by the composer to control pitch transposing, rhythm shifting and stereo panning.

As part of the composing cycle the composer specifies which control signals will make use of the frequency shift information. To bring further direction to a piece, the capability of commanding program changes when a control signal switches ON is also included. Such program changes as changing voices on other control signal related channels can be specified with this capability by the composer.

A simple format is followed to write a song and enter it into the computer. Simple songs can be easily written by beginning users. The writing of more musically complex and sophisticated songs may take more skill. Therefore, precomposed songs including training songs are provided as part of the invention. Once a user selects a song to play, playing the selected song really means playing a synthesizer through control of their brain-body signal. Playing the synthesizer by changing the individual control signals of their brain-body signal is analogous to playing the keys on the keyboard of the synthesizer.

A play music routine is presented in flow diagram form in FIG. 7. Prior to executing the routine, the user selects a template for a piece of previously composed music. At step 701, the process determines whether all of the control signals have been processed during this execution of the play music routine. At process step 702, the routine first determines whether the control signal is being disabled by another control signal. This results from another control, prior to this point, turning on the disable function for this control signal. If so, the remainder of the routine is skipped for this iteration. If not, the status of the control signal is determined at process step 704. The decision step 704 determines whether the signal is above the ON-switch for the first time, whether it has been ON and is now ON, whether the signal is OFF for the first time, or whether it has been OFF and is now OFF. This determination is made in terms of the present magnitude and the past magnitude relative to the ON and OFF switch levels for this control signal.

If the control signal is on for the first time since it was last switched off, at step 706, the routine determines whether the control signal is to be used to cause program changes of other control signals. If so, at process step 708, program change commands such as a change of voice on a specified MIDI channel are sent to the MIDI interface 51 of FIG. 1. If instead, notes are to be played with this control signal, requested pitch transposition, left/right pan and/or rhythm change commands are implemented per step 710. Pitch transposition involves shifting the pitch of the notes to be played on this channel up or down a specified number of half steps times the number of steps the lock-in frequency for this control signal is presently shifted. Rhythm change is also serviced at this time. The rhythm is increased or decreased by an amount proportional to the frequency shift change occurring for this control signal. Likewise, a left/right pan command is sent to the synthesizer to shift the stereo balance proportional to the amount of frequency shift, minus to the left and plus to the right. At step 712, a volume level is computed as a function of the current magnitude of the control signal. A note ON command is sent to the MIDI interface 51 with the desired pitch and newly computed volume per step 714. If a harmony group is to be played by this control signal, pursuant to step 716, the rest of the notes of the harmony group are turned ON. Finally, if this control signal is to disable other control signals while ON, disable switches for those channels are now set per step 718.

Returning to step 704, if this control signal is ON and has been ON prior to this pass through the play music routine, at process step 720, an updated volume level is computed and sent to the MIDI interface. If the notes played with this control signal are to provide a rhythmical pattern and a beat such as 4—4 time, a rhythm routine is serviced at step 722. Rhythm is accomplished by turning the notes ON and OFF and accenting the notes at the appropriate time. A background loop counter is used to determine when notes are to be turned ON and OFF and when to be accented. If the routine at step 720 determines that the control signal is below the OFF switch and it has been OFF prior to this iteration, the play music routine is discontinued. However, if the control signal is below the OFF-switch for the first time, any notes that were turned ON are now turned OFF at step 724. Any disable switches that were set are turned OFF at step 726. Finally the melody string routine is serviced at step 728. This involves selecting the next note to be played when the control signal goes above the ON-switch as detected at step 714.

Figure 8:
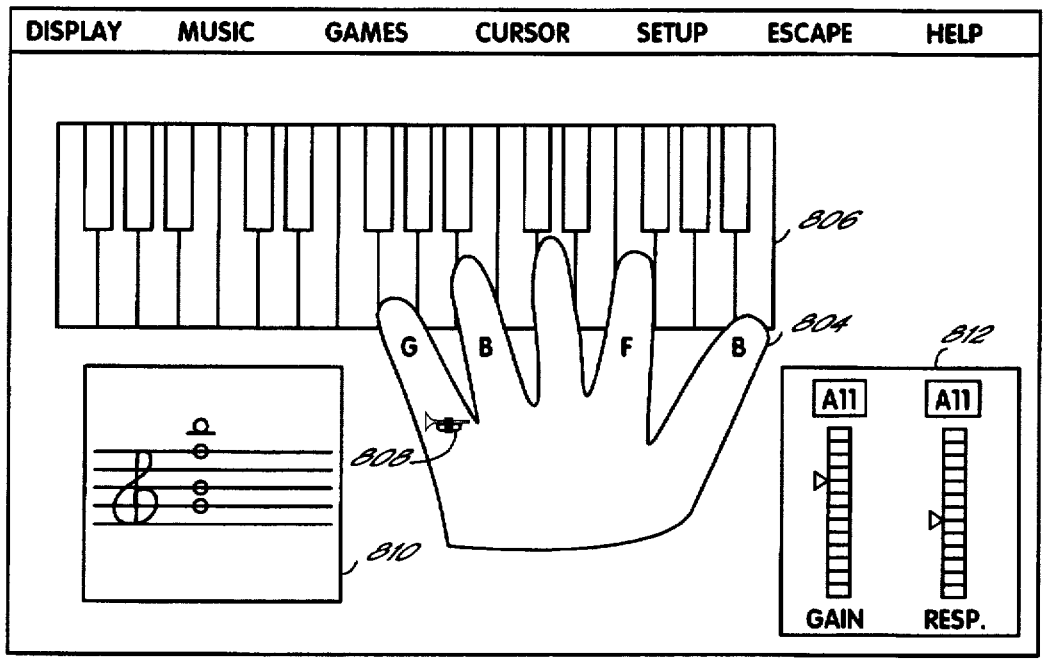
FIG. 8 is a drawing of the musical player/trainer display.

Referring to FIG. 8, the musical player training screen 802 is illustrated and is accessed through the music menu 620. As a control signal goes above a corresponding ON-switch, a graphical finger 804 depresses a keyboard key 806 and an icon 808 appears indicating the note and voice being played. In addition, as the notes are played, they are annotated on a moving musical staff 810. Slide controls 812 are included so that gain and response of the control signals can be changed at any time during the playing of a musical piece.

Figure 9:
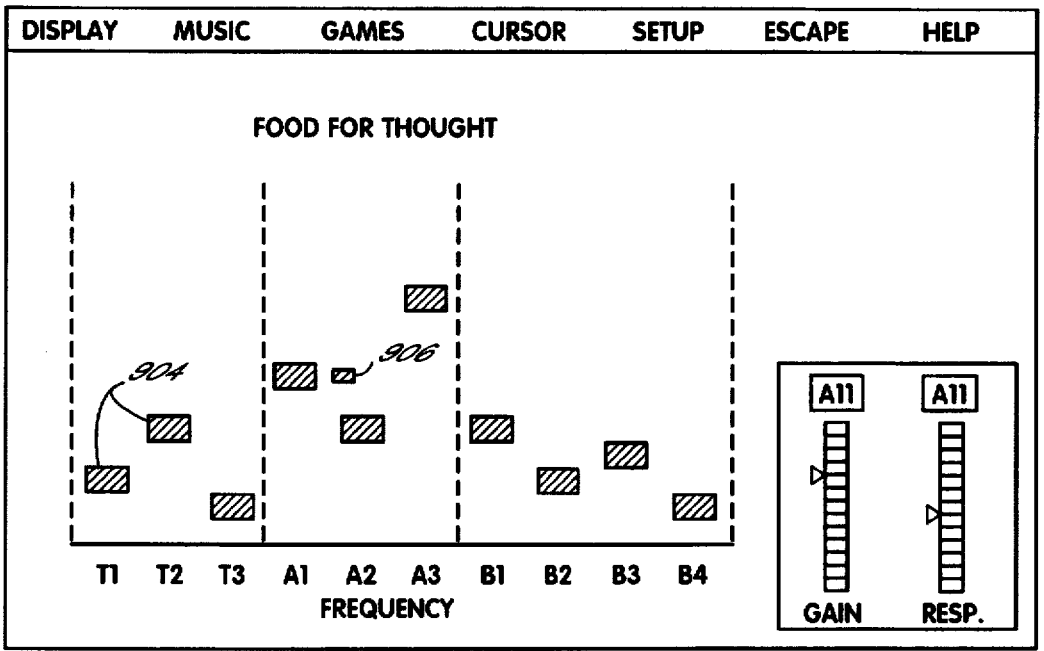
FIG. 9 is a drawing of a graphical display for the training game Food For Thought.

Examples of training games selectable through the game menu 628 are described with reference to FIGS. 9 and 10. These games help the user improve their ability to regulate their brain-body derived control signals. The game "Food For Thought" has the screen 902 illustrated in FIG. 9. The control signals are represented as rectangles 904 that move up and down as a function of their magnitude much like the bar graphs of FIG. 6. A smaller rectangle 906 is preferably driven by a random generator to start at the right side of the screen, and the computer thereafter moves it across the screen from right to left. The rectangle 906 is called the food beam. The user's task is to move a selected control signal rectangle 904 to an appropriate height to intersect the food beam. Audio feedback is provided to reinforce the occurrence of all intersection.

Figure 10:
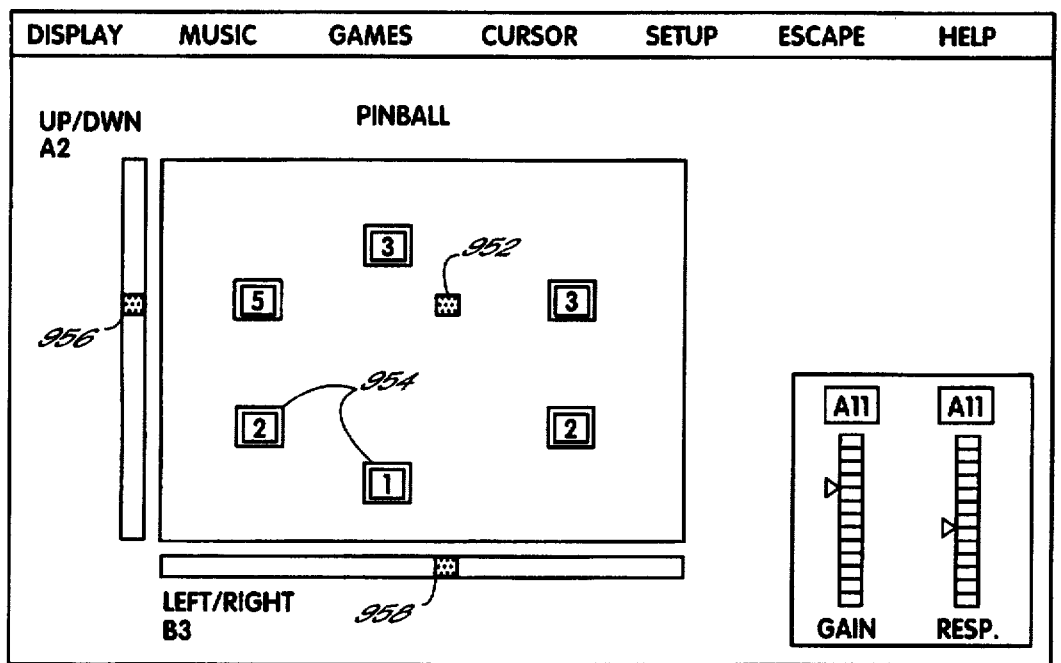
FIG. 10 is a drawing of a graphical display for the training game Pinball.

A second training game "Pinball" has a screen 950 illustrated in FIG. 10. This game trains the user in two axis control. One control signal magnitude causes left/right movement of the pinball 952. A second control signal causes up/down movement of the pinball 952. The user selects which control signals to map to the two axes of the pinball 952. In the illustrated screen 950, the user has chosen the second alpha band control A2 for up/down and the third beta band B3 for left/right control. The magnitude changes of the selected control signal which results in pinball 952 up/down movement of rectangle 956 is also displayed in a side bar 956, as is the control signal magnitude that causes left/right movement of rectangle 958. In a second variation of this pinball game, the user selects a control signal magnitude for up/down movement and the frequency shifting of the control signal for left/right movement. The task of the user is to cause the pinball 952 to intersect with numbered score boxes 954. Playing this game develops two axis control skills. As will be appreciated, other games may be generated which train and develop three axis and other multi-axis skills.

Figure 11:
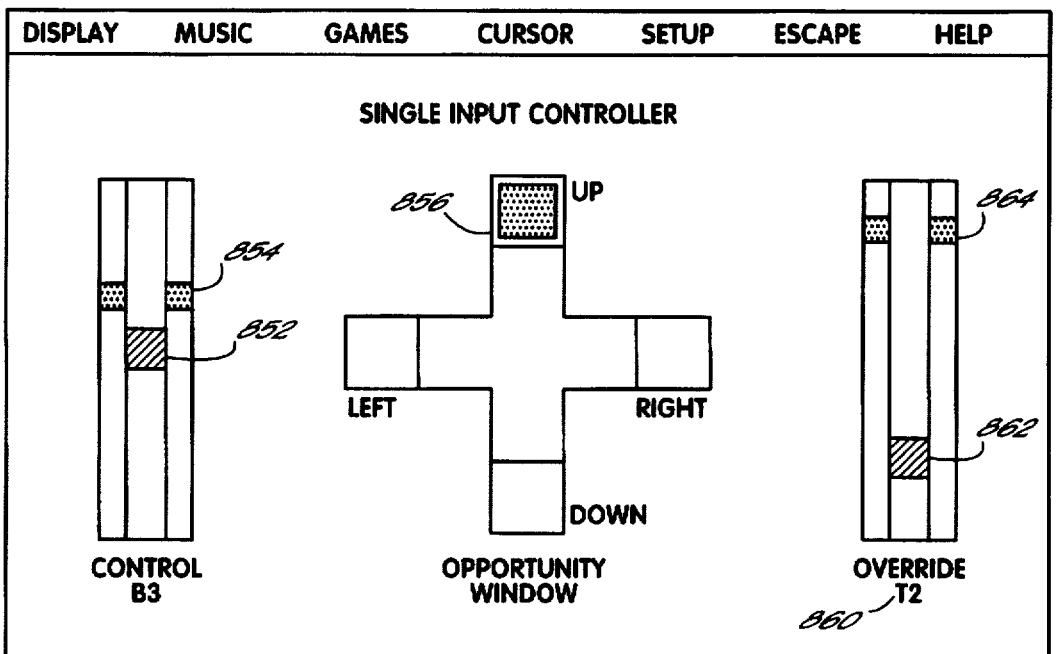
FIG. 11 is a drawing of a graphical display for multi-axis control using a single control signal.

Choosing the cursor menu 630 of FIG. 6 allows the user to access the controller portion of the control system to create an interface to either move a mouse cursor through a maze, use the same mouse cursor to move about a displayed keyboard to make use of a line editor, or interact with external devices. The controllers determine how the control signals are used to permit cursor movement and multi-axis control. FIG. 11 illustrates a screen 850 that may be used to establish limits on the use of one control signal. In this illustration the control signal B3 has been selected by the user to be used as the operative control signal. When the magnitude of B3, as indicated by the center rectangle 852 exceeds the preset ON-switch limit 854, action occurs in the direction indicated by the opportunity window pointer 856, for example, the up direction as illustrated. As long as the B3 control remains ON, action continues in the same direction. When B3 has a magnitude such that the center rectangle 852 is below the ON-switch 854, the action ceases. If no action is commenced by the user, the opportunity window pointer remains in one location for a preselected time interval called the dwell time. After the dwell time has elapsed, the pointer steps to the next direction in a clockwise direction. For the example in FIG. 11, the pointer will step from 'up' to the 'right'. in this way, the pointer automatically steps through each of the opportunity window directions. By synchronizing their ON-OFF movements with the location of the opportunity window pointer the user can actuate the desired two axes. The dwell time of the opportunity window is user selectable. If the controller is interfaced to the mouse cursor, the controller selected action translates into cursor movement in the selected direction. If the controller is interfaced to an external device the controller selection causes a switch closure or an analog voltage change resulting in a movement or action of the external device in the appropriate direction.

A second control signal is used as an override switch 860. When the override rectangle 862 exceeds the preset ON-switch limit 864, the override is initiated. The purpose of the override switch is to limit movement when the user generates a brain-body signal component which indicates inattentiveness or distraction. Body movements resulting from inattentiveness or distraction often cause large control signal magnitude and phase changes, especially in the low frequency range. The override band is useful, for example, in the control of a wheelchair was being performed. For wheelchair control, the up/down 856 labels are replaced with forward and backward labels. The mapping of the control signals to the control and override bands and values for the ON switches are user selectable.

Figure 12:
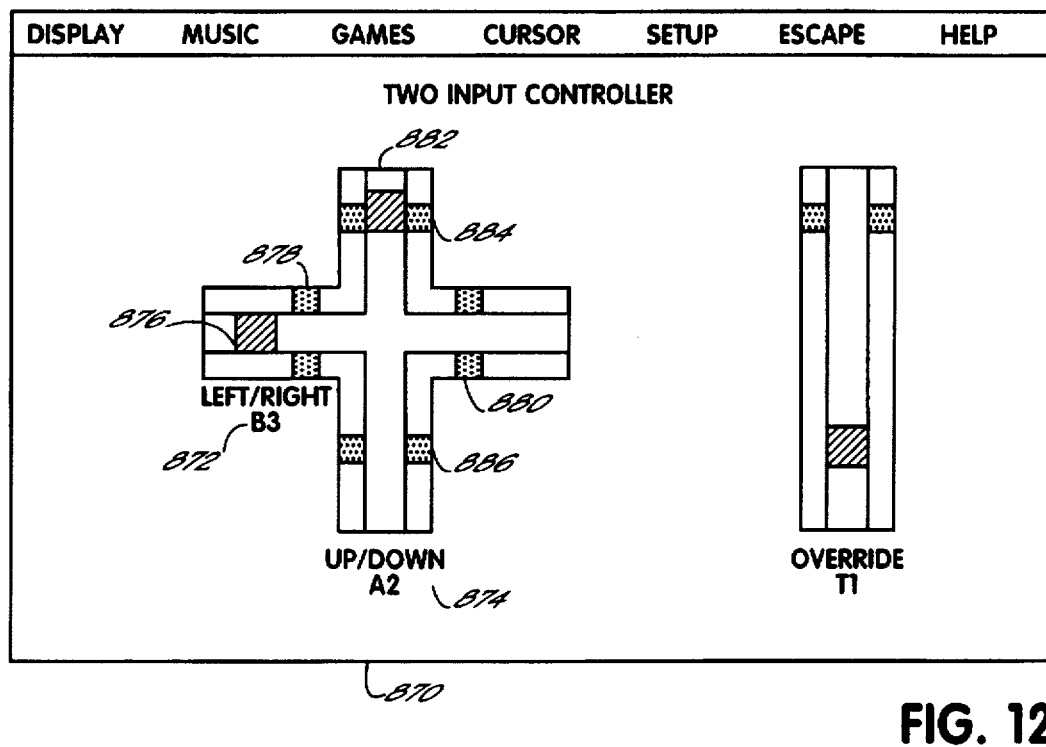
FIG. 12 is a drawing of a graphical display for multi-axis control using two control signals.

FIG. 12 illustrates a screen 870 which allows the use of two control signals to achieve two axis control. In this illustration, the user has selected the B3 control signal for left/right movement as indicated at 872, and the A2 control signal for up/down movement as indicated at 874. In the case of left/right movement, a left direction motion is initiated when the control signal magnitude B3 goes low moving left/right rectangle 876 left of the left switch limit 878. A right direction motion is initiated if an increasing magnitude of the B3 control signal moves the left/right rectangle 876 to the right of the right switch limit 880. When the B3 control signal magnitude goes low, the magnitude pointer, or left/right rectangle 876, moves left; and when the B3 control signal magnitude goes high, the left/right rectangle 876 moves right. A similar paradigm is employed for the up/down movement. For example, an increase in magnitude of the A2 control signal causes the up/down pointer 882 to move up. When the pointer 882 crosses the ON-switch limits 884 or 886, the appropriate action, up or down, is initiated. Exceeding the ON-switch limits may be used to move the mouse cursor or open and close switches. Running weighted averages for each of the control signals are computed for each iteration of the routine. These running weighted averages are additional lowpass filters and are used to offset the motion of the rectangles 876 and 882 so that, on average, the control signals appear in the center of the two axis display. In this way, on average, control action in any direction is equally possible. The previously described feature is user selectable. Control signal frequency shifting can also be selected by the user to drive the up/down or left/right rectangles 876 and 882. A typical paradigm is for a user is to use the magnitude of a control signal for up/down movement and to use the frequency shifting of the control signal for left/right movement. An override band is also available as part of the two controller routine and operates similarly to the override band 860 of FIG. 11. Control signal mapping and on switch locations are user selectable.

Figure 13:
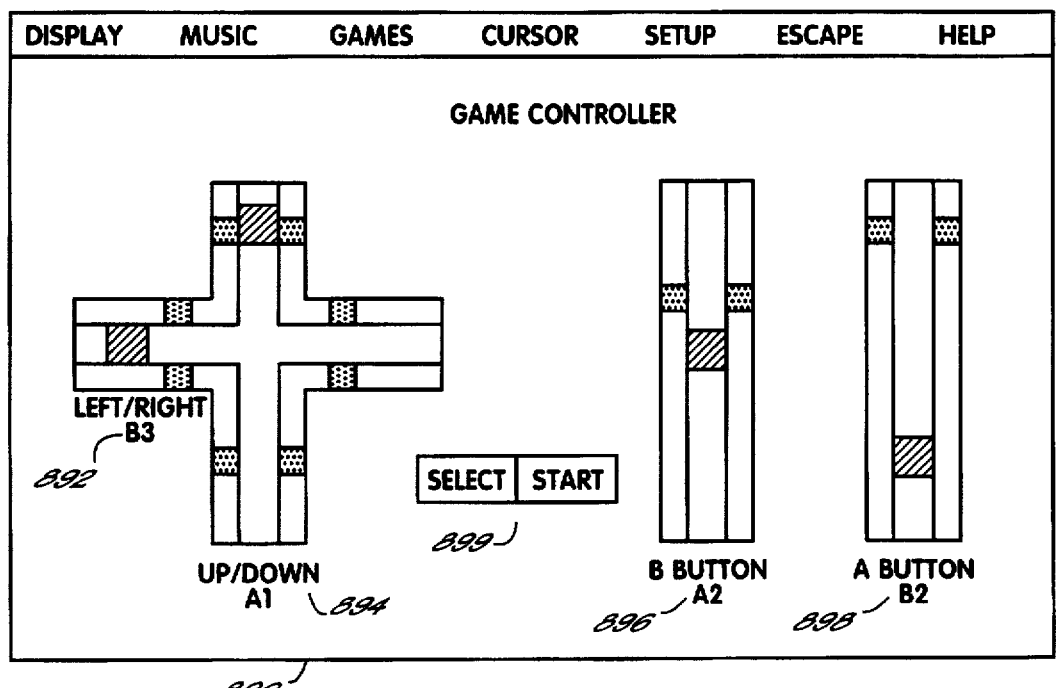
FIG. 13 is a drawing of a graphical display for a video game controller.

A video game controller 890 is illustrated in FIG. 13. The same controller paradigms discussed above are utilized here. In addition to the two axis controller for left/right rectangle 892 and up/down rectangle 894, two other control signals are used to control an equivalent to the B button 896 and the A button 898 functions found on many video game controllers. Select and start 899, are under mouse and keyboard control.

The lock-in amplifier allows a continuous wave or steady state analysis approach for working with the brain-body signal. This yields magnitude and phase values at selected frequencies. Because the claimed invention works with both EEG and EMG biopotentials within the accepted EEG frequency range of interest, the user is able to utilize both the EEG and EMG to affect control. Additionally, transient wave activity resulting from large EMG signals is available to affect control. For example, for most users, looking hard right then center causes the brain-body signal to reach a maximum limit. This pattern can be recognized by the invention. Making use of this fact, the user may define an event which initiates a system command when the user looks hard right or hard left a user defined number of times. The user enters the setup routine to define special transient events and to calibrate the user's transient movements. This capability of recognizing special events is useful for differently abled users or for users engaged in tasks who find themselves unable to actuate other input devices 20 of FIG. 1.

As will be appreciated, the invention may have many variations from that just described. For example, in addition to the electrodes, the amplifier and filter and a battery power supply may be mounted in a headband worn by the subject. While it is convenient to detect both EEG and EMG activity at the forehead, it is also possible to detect those biopotentials at different locations and still process the potential signals in the same way to achieve the same result. Even though EEG biopotentials must be detected on the head, EMG biopotentials may be detected anywhere on the body where muscle activity is proximate. Of course this results in additional system complexity and more connections to the user. In a clinical, educational or research setting this may be appropriate. However, as a mass market device, the disclosed embodiment with only one measurement site has many advantages. The disclosed embodiment utilizes a frequency range of 0.5 Hz to 45 Hz within which the control signals may be chosen. It is contemplated that the frequency range in which manifestations of both EEG and EMG may be found is 0.5 Hz to 500 Hz, and therefore, the control system may be designed to select control signals within the 0.5 Hz to 500 Hz range. The signal processing of the control system has been described with regard to the processing EEG and EMG. However, as will be appreciated by those who are skilled in the art, the disclosed lock-in amplifier and phase-locked loop approach may be used for other applications, such as analysis and control of vibration frequencies, or other real world signals. While the control system has been described as utilizing an input signal created by a human, the control system may also be utilized with animals, machines other sources of input signals having a relatively low signal to noise ratio and a pseudo random periodicity.

The invention has been described with control signal generation accomplished using a lock-in amplifier approach. It will be appreciated by those skilled in the art that other signal transform techniques can be utilized to obtain control signals and to create phase-locked loops. For example, the magnitude and phase information at the reference frequencies can also be obtained from an FFT of the brain-body signal.

It should be further noted that the use of ten control signals is arbitrary. Any number of control signals, such as, for example, 50, may be used to practice the invention. Further, frequency range in which the control signals may be selected is also arbitrary. While it is advantageous to keep the frequency range below 60 Hz, such is not mandatory with current filter technology.

It is well within the skill of those in the art to code programs following the steps of the flowcharts described herein. In the preferred embodiment, QUICK BASIC 4.5 and a BASIC compiler which are commercially available on DOS based machines may be used to implement the claimed control system.

While the invention has been illustrated in some detail according to the preferred embodiments shown in the accompanying drawings and while the preferred embodiments have been described in some detail, there is no intention to thus limit the invention to such detail. On the contrary it is intended to cover all modification, alterations and equivalents falling within the spirit and scope of the appended claims.

What is claimed is:

1. A method of controlling a device in response to biopotentials produced by a user, the method comprising the steps of:

providing a control signal having a reference frequency;

detecting the biopotentials;

producing in response to detecting the biopotentials an input signal changing as a function of changes in the biopotentials;

sampling the input signal at successive sample times to produce sampled input signals over successive sample times; and periodically computing X and Y quadrature values at the reference frequency of the control signal for the sampled input signals;

periodically computing averaged X and Y quadrature values by averaging the X and Y quadrature values for the sampled input signals with moving average time windows, said moving average time windows averaging the X and Y quadrature values over a selectable length of time adaptable to a user; and periodically computing an averaged magnitude of the control signal in response to the averaged X and Y quadrature values, the averaged magnitude of the control signal being associated with the reference frequency and changing as a function of both changes in magnitude of the biopotentials and the selectable length of time;

presenting to the user a representation of the averaged magnitude of the control signal to enable the user to sense the changes of the magnitude of the biopotentials; and controlling the device as a function of the changes of the magnitude of the biopotentials.

2. The method of claim 1 wherein the step of periodically computing averaged X and Y quadrature values further comprises the step of adjusting the selectable length of time of the moving time average windows, thereby adapting to the user a rate of change of the averaged X and Y quadrature values in response to changes in the biopotentials.

3. A method of controlling a device in response to biopotentials produced by a user, the method comprising the steps of:

providing a control signal having a reference frequency;

detecting the biopotentials;

producing in response to detecting the biopotentials an input signal changing as a function of changes in the biopotentials;

sampling the input signal at successive sample times to produce sampled input signals over successive sample times; and periodically computing X and Y quadrature values at the reference frequency of the control signal in response to the sampled input signals;

periodically computing over a user selectable length of time averaged X and Y quadrature values by averaging the X and Y quadrature values; and periodically computing an averaged magnitude of the control signal in response to the averaged X and Y quadrature values, the averaged magnitude of the control signal being associated with the reference frequency and changing as a function of changes in magnitude of the biopotentials and the user selectable length of time;

presenting to the user a representation of the averaged magnitude of the control signal to enable the user to sense the changes of the magnitude of the biopotentials; and controlling the device as a function of the changes of the magnitude of the biopotentials.

4. The method of claim 3 wherein the step of periodically computing averaged X and Y quadrature values further comprises the step of providing an input adaptable for use by the user to adjust the user selectable length of time, thereby adapting to the user a rate of change of the averaged X and Y quadrature values in response to changes in the biopotentials.

5. A method of controlling a device in response to biopotentials produced by a user, the method comprising the steps providing a control signal having a reference frequency detecting the biopotentials;

producing in response to detecting the biopotentials an input signal changing as a function of changes in the biopotentials;

sampling the input signal at successive sample times to produce sampled input signals over successive sample times; and establishing a base phase value of the control signal at the reference frequency in response to one of the sampled input signals;

periodically computing time averaged phase values of the control signal in response to subsequent sampled input signals each of the time averaged phase values representing an average frequency of the biopotentials within a predetermined bandwidth of frequencies with respect to the reference frequency;

periodically comparing each of the time averaged phase values to the base phase values;

periodically changing the reference frequency as a function of comparing the time averaged phase values to the base phase values, the reference frequency changing as a function of changes of the average frequency of the biopotentials;

establishing a new base phase value of the control signal in response to the changing reference frequency;

presenting a representation of the changing reference frequency to the user to enable the user to sense the changes of the average frequency of the biopotentials; and controlling the device as a function of the changes of the average frequency of the biopotentials.

6. A method of controlling a device in response to biopotentials produced by a user, the method comprising the steps of:

providing a control signal having a reference frequency detecting the biopotentials;

producing in response to detecting the biopotentials an input signal changing as a function of changes in the biopotentials;

sampling the input signal at successive sample times to produce sampled input signals over successive sample times; and periodically computing X and Y quadrature values at the reference frequency of the control signal for the sampled input signals;

periodically computing time averaged X and Y quadrature values by averaging the X and Y quadrature values for the sampled input signals in moving average time windows; and periodically computing time averaged phase values in response to the time averaged X and Y quadrature values, each of the time averaged phase values of the control signal representing an average frequency of the biopotentials with respect to the reference frequency;

periodically changing the reference frequency as a function of the time averaged phase values of the control signal, the reference frequency changing as a function of changes of the average frequency of the biopotentials;

presenting representations of the changes of the reference frequency to the user to enable the user to sense the changes of the average frequency of the biopotentials; and controlling the device as a function of the changes of the average frequency of the biopotentials.

7. A method of presenting representations of biopotentials produced by a user, the method comprising the steps providing a control signal having a reference frequency:

detecting the biopotentials;

producing in response to detecting the biopotentials an input signal changing as a function of changes in the biopotentials;

sampling the input signal at successive sample times to produce sampled input signals over successive sample times;

periodically computing magnitude and phase values at reference frequency of the control signal in response to the sampled input signals;

averaging over a selectable length of time adaptable to a user the magnitude and phase values to produce averaged magnitude and averaged phase values of the control signal changing in response to changes in magnitude and frequency of the biopotentials and the selectable length of time; and producing representations to the user of changes of the averaged magnitude and averaged phase values of the control signal to enable the user to sense changes in the biopotentials.

8. An apparatus for controlling an external device in response to biopotentials produced by a user, the apparatus comprising:

a sensor adapted to be mounted on the user for producing an input signal in response to detecting the biopotentials produced by the user, the input signal changing as a function of changes in the biopotentials;

a digital signal processor operatively connected to the sensor and periodically sampling the input signal, the digital signal processor providing a control signal having a reference frequency and including a digital lock-in amplifier means for periodically computing X and Y quadrature values at a reference frequency of the control signal in response to periodic samples of the input signal, periodically computing over a selectable length of time adaptable to a user averaged X and Y quadrature values in response to the X and Y quadrature values with a digital moving average time window filter, and periodically computing a magnitude value of the control signal at the reference frequency in response to the averaged X and Y quadrature values, the magnitude of the control signal changing as a function of changes in magnitude of both the biopotentials and the selectable length of time;

an output device connected to the signal processor and providing a representation to the user of the magnitude of the control signal to enable the user to sense changes in the magnitude of the control signal as a function of changes in the magnitude of the biopotentials; and a controller operatively connected to the signal processor and the external device for controlling the external device as a function of changes in the magnitude of the biopotentials.

9. An apparatus for controlling an external device in response to biopotentials produced by a user, the apparatus comprising:

a sensor adapted to be mounted on the user for producing an input signal in response to detecting the biopotentials produced by the user, the input signal changing as a function of changes in the biopotentials;

a digital signal processor operatively connected to the sensor and periodically sampling the input signal, the digital signal processor providing a control signal having a reference frequency and including a digital lock-in amplifier means for periodically computing X and Y quadrature values at the reference frequency of the control signal in response to periodic samples of the input signal, periodically computing averaged X and Y quadrature values in response to the X and Y quadrature values, and periodically computing a phase value of the control signal at the reference frequency in response to the averaged X and Y quadrature values, the phase value of the control signal changing as a function of changes in frequency of the biopotentials, the digital signal processor further including a digital phase locked loop responsive to the phase value of the control signal for changing a frequency of the reference frequency as a function of a change of the phase value of the control signal;

an output device connected to the signal processor and providing representations of the frequency of the reference frequency to the user to enable the user to sense changes in the frequency of the reference frequency as a function of changes of the frequency of the biopotentials; and a controller operatively connected to the signal processor and the external device for controlling the external device in response to the changes of the frequency of the biopotentials.

10. An apparatus for presenting representations of biopotentials produced by a user, the apparatus comprising:

a sensor adapted to be mounted at a single location on the user for producing an input signal in response to detecting the biopotentials produced by the user, the input signal changing as a function of changes in the biopotentials;

a digital signal processor operatively connected to the sensor and periodically sampling the input signal, the digital signal processor providing a control signal having a reference frequency and including a digital lock-in amplifier means for periodically computing X and Y quadrature values at the reference frequency of the control signal in response to periodic samples of the input signals, periodically computing over a user selectable length of time averaged X and Y quadrature values in response to the X and Y quadrature values with a digital moving average time window, and periodically computing a magnitude value and a phase value of the control signal at the reference frequency in response to the averaged X and Y quadrature values, the magnitude and phase values of the control signal changing as a function of changes in magnitude and frequency of the biopotentials and the user selectable length of time, the digital signal processor further including a digital phase locked loop responsive to the phase value of the control signal for changing a frequency of the reference frequency as a function of a change of the phase value of the control signal; and an output device connected to the signal processor for presenting representations of the magnitude of the control signal and the frequency of the reference frequency to the user to enable the user to sense changes in the magnitude and the frequency of the biopotentials.

* * * * *